United States Patent [19]
Koga et al.

[11] Patent Number: 5,847,224
[45] Date of Patent: Dec. 8, 1998

[54] METHOD FOR IMPROVING THE COLOR OF MTBE, ETBE AND TAME

[75] Inventors: Kunio Koga; Misao Mori, both of Houston, Tex.

[73] Assignee: Global Octanes Corporation, Houston, Tex.

[21] Appl. No.: 494,235

[22] Filed: Jun. 23, 1995

[51] Int. Cl.$^6$ .................................................. C07C 41/34
[52] U.S. Cl. ............................................................ 568/699
[58] Field of Search ............................................. 568/699

[56] References Cited

U.S. PATENT DOCUMENTS

| | | | |
|---|---|---|---|
| 2,065,540 | 12/1936 | Schneider | 260/106 |
| 2,474,874 | 7/1949 | Van Der Hoeven | 260/616 |
| 2,679,459 | 5/1954 | Rosenwald | 99/163 |
| 3,940,450 | 2/1976 | Lee | 260/614 |
| 4,714,788 | 12/1987 | Michaelson et al. | 568/69 |
| 4,731,489 | 3/1988 | Whisenhunt et al. | 568/697 |
| 4,740,633 | 4/1988 | Boitiaux et al. | 568/699 |
| 5,084,070 | 1/1992 | Kohler et al. | 568/699 |
| 5,158,652 | 10/1992 | Pucci et al. | 568/699 |
| 5,321,163 | 6/1994 | Hickey et al. | 568/59 |
| 5,382,707 | 1/1995 | Rubin et al. | 568/697 |

*Primary Examiner*—Marianne M. Cintins
*Assistant Examiner*—Dwayne C. Jones
*Attorney, Agent, or Firm*—Mark A. Tidwell; Robert C. Curfiss

[57] ABSTRACT

A process for improving the color of oxygenates, such as MTBE, ETBE and TAME, which utilizes a hydrogenation treater in the presence of a catalyst, containing at least one noble metal, along with a circulation of hydrogen to remove the color. The process reduces existing color bodies in the oxygenate and may proceed at room temperature and at normal pressure for economically providing a completely clear product having a +30 saybolt number.

27 Claims, 3 Drawing Sheets

METHOD FOR IMPROVING THE COLOR OF MTBE, ETBE AND TAME

BACKGROUND OF INVENTION

1. Field of Invention

This invention is generally related to a process for the production of gasoline blending oxygenate components, such as MTBE, ETBE and TAME, and is specifically directed to a method for improving the product color of MTBE, ETBE and TAME.

2. Description of the Prior Art

Methyl tertiary butyl ether (MTBE), ethyl tertiary butyl ether (ETBE), and tertiary amyl methyl ether (TAME) are well recognized as gasoline blending components. These components are desirable because they have a high octane value and the oxygen in the molecular structure facilitates effective combustion of gasoline while suppressing carbon monoxide formation. The use of MTBE in gasoline for the protection of environment and octane value improvement has made it the fastest growing large volume chemical in the world.

MTBE is produced through the reaction of isobutylene with methanol over a catalyst. ETBE can be basically produced by changing the alcohol feedstock from methanol to ethanol. TAME is similarly produced through the reaction of isoamylene with methanol over a catalyst. The isobutylene necessary for producing MTBE and ETBE can be obtained from various sources. A common source for isobutylene is through the dehydrogenation of isobutane. The dehydrogenation of isobutane to produce isobutylene is a highly endothermic reaction and proceeds at a high temperature of above 1100 degrees Fahrenheit because of the limitation in thermodynamic equilibrium.

The isoamylene necessary for producing TAME is usually obtained through a process similar to the dehydrogenation process for obtaining isobutylene. Typically, isoamylene is obtained from a Fluidized Catalytic Cracking (FCC) unit in which hydrocarbon cracking reactions proceed. Isoamylene is removed from the bottom of a distillation column of the FCC unit. The catalytic dehydrogenation of isobutane occurs through a complex reaction pattern with many cracking side reactions resulting in the formation of heavy materials, aromatic compounds and the like. The same reactions occur in the production of isoamylene. Thus, the reactions to produce isobutylene and isoamylene include many cracking side reactions which promote the production of carbonaceous deposits, including cyclic compounds at the activated sites of catalysts.

Because the product of the reaction process is recovered from the depropanizer bottom, it contains the carbonaceous deposits, including the higher boiling compounds, which are produced in the reaction area. These higher boiling compounds are considered to be mainly multiple ring aromatic compounds. It is believed that a portion of these multiple ring compounds have a color which causes the end product to have a yellowish color. A saybolt number is used to indicate the color intensity or degree of color in the product. A saybolt number of +30 indicates that the product has no color or is completely clear, like water. As the saybolt number decreases, the color in the product increases. Typically, untreated MTBE has an average saybolt number of +18 and appears slightly yellow. However, the saybolt number may vary from +16 to +20 depending on the reaction plant operation conditions. Untreated ETBE and TAME typically show much lower saybolt numbers than MTBE, such as +7 and +6, respectively.

Due to the increasing concern for the protection of the environment and the public's belief that a clear product is analogous to a "clean" or "environment friendly" product, it has become increasingly desirable for companies to produce and advertise a clear or "clean" gasoline for sale. In addition, a clear product is desirable because it does not contaminate the engine room or exhaust line. A product having color indicates that the product includes various chemicals having double bonds in their structure. These double bonds are relatively susceptible to forming polymers which make the engine room and exhaust line dirty. Thus, it is important that the gasoline blending components, such as MTBE or ETBE, be as colorless as possible in order to maintain "clean" gasoline. Typically, MTBE and ETBE must be treated to upgrade the color of the product to meet the requirements of various companies for a clear or "clean" MTBE and ETBE. Therefore, it is desirable for suppliers to have an economical method for treating gasoline blending oxygenate components, such as MTBE, ETBE and TAME to produce a completely clear product.

Generally, there are ways to improve the color of MTBE and ETBE, such as activated carbon treatment and evaporation processes. However, known methods for treating the product to improve color may be expensive, incurring ongoing expenses such as steam consumption in the evaporation process and carbon usage in the activated carbon treatment method, and a carbon bed may not achieve the desired clear product having a +30 saybolt number for a long period. The activated carbon treatment method removes color in the product by adsorption of the color bodies in the MTBE and ETBE. However, in order to try to achieve +30 saybolt color using an activated carbon filter operation, the level of activated carbon consumption is high and relatively expensive.

Therefore, there is a need for a method for improving the color of gasoline blending components which provides a completely clear product, is economical and long-lasting, and may operate at normal temperature and pressure.

SUMMARY OF THE INVENTION

The subject invention is directed to a method for improving the color of oxygenates, such as MTBE, ETBE and TAME, by reducing the color bodies to economically provide a colorless product. The subject invention utilizes a hydrogenation technology by which the color bodies existing in the oxygenate can be hydrogenated under room temperature and normal pressure conditions to completely remove color. The hydrogenation can be successfully accomplished with any type of hydrogenation treater, such as, packed bed reactor like trickle bed with liquid dispersion, packed bed with gas dispersion, perfectly stirred tank with gas bubbling and the like. The subject invention was developed after an extensive evaluation to identify the color bodies causing the color in the product and is specifically designed to provide gasoline blending components, such as MTBE, ETBE and TAME with a color intensity having a +30 saybolt number. A saybolt number measures the color intensity using lower numbers to indicate poor color quality and a highest rating of +30 to indicate a completely clear product.

In the preferred embodiment, the untreated product is fed to a trickle bed reactor while hydrogen is simultaneously fed to the reactor. The trickle bed reactor of the preferred embodiment is packed with 0.5 wt % of Pd/r-alumina catalyst. While Pd/r-alumina is preferred, most of the general hydrogenation catalysts, such as palladium/carbon, palladium/silica, palladium/alumina, platinum/carbon, platinum/silica, platinum/alumina, raney-Ni and the like, can be utilized. Also, the amount of the preferred catalyst may range from 0.1 weight percent to 5 weight percent palladium/r-alumina. The necessary amount of catalyst and the reactor volume is determined by the feed rate of the product and the desired color intensity. The MTBE, ETBE or TAME is fed into the reactor along the catalyst surface concurrently with a circulation of hydrogen and the hydrogenation reaction proceeds at room temperature and normal pressure. The treated product recovered at the bottom of the trickle bed is completely clear and shows a color intensity having a +30 saybolt number.

In another embodiment, the hydrogenation is accomplished using a stirred tank reactor with gas bubbling. A catalyst, preferably 2.5% Pd/r-alumina, is fed into the product in a slurry reactor with a stirrer. After stirring, the catalyst is separated by precipitation and new product is added in the same slurry reactor. Hydrogen is then bubbled, stirring the liquid phase at room temperature and normal pressure. This procedure completely eliminates color and produces MTBE, ETBE or TAME having a +30 saybolt number.

The subject invention provides a method for economically treating oxygenates, such as MTBE and ETBE, to meet +30 saybolt number color specifications. The productivity of the trickle bed reactor is high because the flooding velocity is sufficient. While catalyst cost is low, a key factor of the subject invention in providing an economical method for improving color is the catalyst life. The fact that MTBE and ETBE do not have any poison chemicals contributes to the catalyst life which is predicted to be longer than two years.

In addition, the hydrogen consumption in the process of the subject invention is negligible. In fact, the hydrogen consumed increases the end product weight and is sold as a portion of the product. Another advantage of the hydrogenation method of the invention is that most of the olefine in the oxygenates treated in accordance with the subject invention are changed to paraffins. Thus, there is a big difference in GC chart between non-treated product and treated product.

Therefore, it is an object and feature of the subject invention to provide a method for improving the color properties of oxygenates, such as MTBE, ETBE and TAME, for economically producing a completely clear product.

It is another object and feature of the subject invention to provide a color improvement system utilizing a hydrogenation method for reducing the color bodies in the product to improve color intensity and achieve +30 saybolt number.

It is a further object and feature of the subject invention to provide a color improvement system utilizing a hydrogenation method which may proceed at room temperature and at normal pressure for economically providing a completely clear product.

It is also an object and feature of the subject invention to provide a hydrogenation method utilizing a trickle bed reactor packed with a Pd/r-alumina catalyst for completely and economically removing color from MTBE, ETBE and TAME.

It is yet another object and feature of the subject invention to provide a hydrogenation method utilizing a stirred tank reactor and Pd/r-alumina catalyst for improving the saybolt number of the product to +30.

Other objects and features will be readily apparent from the accompanying drawings and description.

DETAILED DESCRIPTION OF THE DRAWINGS

The subject invention is directed to a color improvement system for improving the color of oxygenates, such as MTBE, ETBE and TAME, by reducing the color bodies therein through hydrogenation to produce a completely colorless product. The color improvement system is a hydrogenation method which economically removes color completely thereby improving the color intensity and achieving a saybolt color number of +30.

Figure 1:
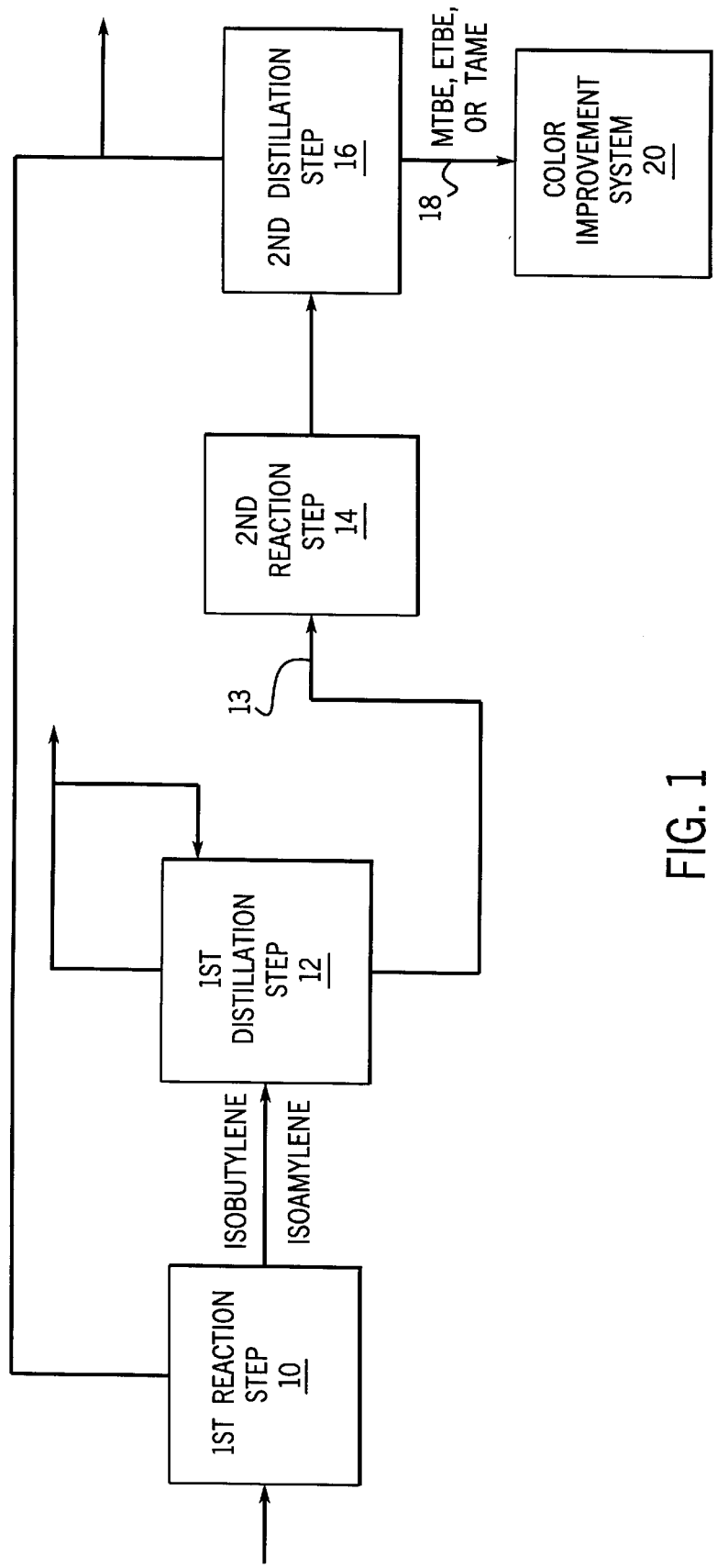
FIG. 1 is an overview of the general steps involved in the production of oxygenates, such as MTBE, ETBE and TAME, including the color improvement system of the subject invention.

As shown in FIG. 1, the process generally begins with a first reaction step 10 in which isobutane is converted to isobutylene. The reaction step 10 is followed by a first distillation step 12 in which the isobutylene necessary to produce MTBE and ETBE is recovered from the depropanizer bottom and the isoamylene necessary to produce TAME is recovered from the bottom of a distillation tower of a FCC unit. The recovered product is then fed to a second reaction step 14 in which MTBE is produced through the reaction of the isobutylene with methanol over a catalyst, ETBE is produced by changing the alcohol feedstock from methanol to ethanol or TAME is produced through the reaction of isoamylene with methanol. The reactor product is sent to a second distillation step 16 and the product is recovered at 18 and fed to the color improvement system 20.

Figure 2:
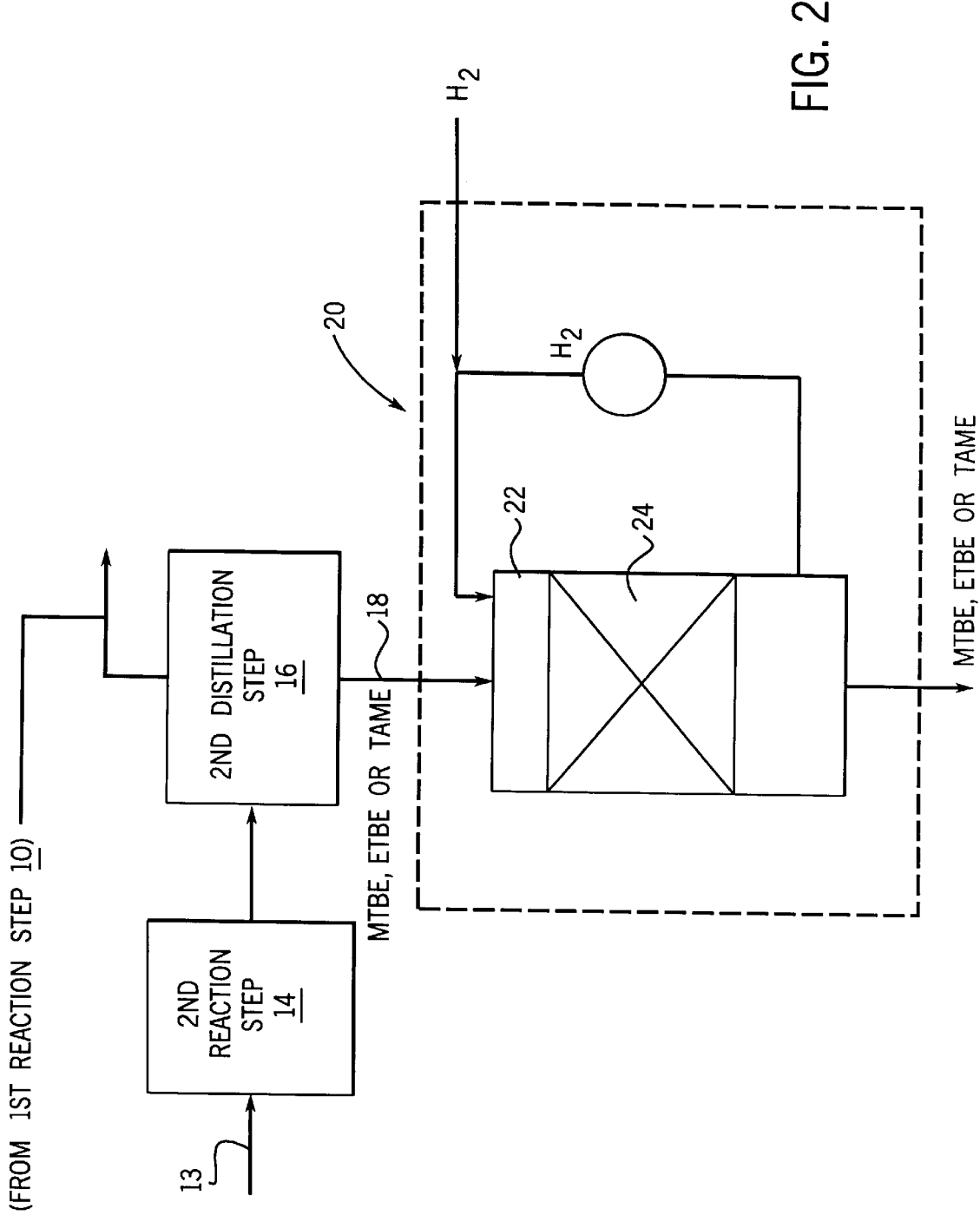
FIG. 2 is a flow chart of the process of the preferred embodiment of the invention utilizing a trickle bed reactor with a Pd/r-alumina catalyst and a circulation of hydrogen to hydrogenate the color bodies in the product fed through the reactor.
Figure 3:
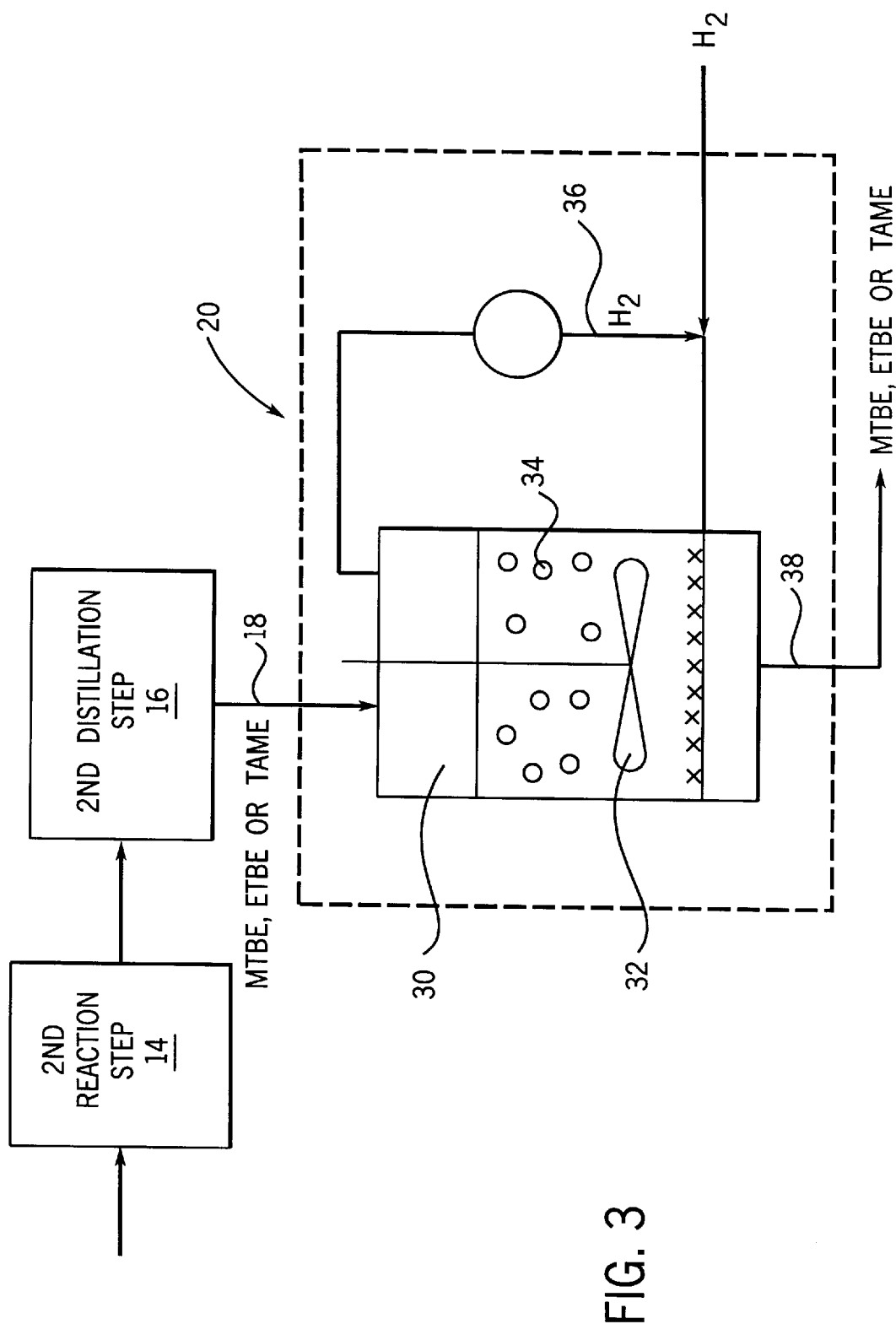
FIG. 3 is a flow chart of the process of another embodiment of the invention utilizing a slurry reactor with a stirrer in which a catalyst is initially stirred with the product and hydrogen is bubbled in the mixture to hydrogenate the color bodies in the MTBE, ETBE, or TAME.

In the preferred embodiment, the color improvement system 20 consists of a trickle bed reactor 22 packed with a catalyst 24. While the catalyst 24 is preferably Pd/r-alumina, most of the general hydrogenation catalysts, such as palladium/carbon, palladium/silica, palladium/alumina, platinum/carbon, platinum/silica, platinum/alumina, raney-Ni and the like, can be utilized. Specifically, the catalyst contains at least one noble metal catalyst selected from the group consisting of ruthenium, rhodium, palladium, iridium, platinum on the carrier like carbon, alumina, silica, zeolite and the like. In addition, raney-Ni is also available for the subject invention. MTBE, ETBE or TAME is fed to the reactor 22 with a circulation of hydrogen 26 (see FIG. 2). The product recovered at 28 is completely clear and meets +30 saybolt color specifications. In another embodiment shown in FIG. 3, the color improvement system 20 consists of a slurry reactor 30 with a stirrer 32 in which a catalyst 34 is stirred and hydrogen 36 bubbled into the mixture to produce a completely colorless product at 38 with a +30 saybolt color number.

In order to develop the subject invention, it was necessary to undertake an extensive and detailed analysis to determine the heretofore unknown color causing substances in oxygenates, such as MTBE, ETBE and TAME. To this end, MTBE was analyzed in detail by Gas Chromatography and Mass Spectre (GC-MS) and High Performance Liquid Chromatography (HPLC) and some color causing substances were found. Unfortunately, due to the extremely low concentration of the color causing substances, in the lower level of ppm or ppb, it was impossible to specifically identify the color causing compounds.

While the theory of color development is unclear, it is well known that some olefine have conjugated double bonds in their molecular structure which may cause color. Thus, it was deduced that some aromatic compounds in the MTBE were causing the color. Based on this assumption, all of the aromatic compounds listed in the analytical results of the tested MTBE were checked for color. After a lengthy evaluation, it was concluded that the color causing compounds were multiple ring aromatic compounds, mainly acenaphthylene and its derivatives, methylene indene and ethylidene indene, and their derivatives. These compounds have a yellow color themselves and are calculated to be present in the range of 10–300 ppm in MTBE. While other compounds having color themselves were noted in the analysis, their concentration is extremely low, in the ppb level, and considered too insignificant to contribute to the color of MTBE.

After it was determined that acenaphthylene and its derivatives, methylene indene and ethylidene indene and their derivatives caused the yellow color, the focus turned to finding a way to remove the color from the product. Three different methods were considered. In the first method, the color bodies are removed, for example, by adsorption in an activated carbon treatment method. While this method may be effective, the required activated carbon usage to achieve +30 saybolt color number is very expensive, especially considering the high level of activated carbon consumption required to reach the desired results. Another method for removing color is by oxidation of the color bodies. However, oxidation technology failed to remove color and, in one experiment utilizing potassium permanganate, turned the liquid yellow color to black.

Finally, a third way to remove color is by reduction of the color bodies. To this end, it was noted that the color causing compounds, acenaphthylene, methylene indene and ethylidene indene, are unsaturated compounds having a conjugated double bond in their molecular structure which presumably gives them color. The structure of these compounds is as follows:

In contrast, saturated compounds like acenaphtene, methyl indene and ethyl indene do not have any color and have the following structure: Therefore, it appeared that if the double bond outside of the benzene structure which have color bodies in their structure could be opened, the color should disappear. Experiments were first conducted in the laboratory using diborane to open these double bonds. At room temperature and normal pressure, 10 cc of BH3/THF solution having a concentration of 1 mol/l was added to 100 g of MTBE having +18.5 saybolt number. The saybolt number, which rates color quality using numerical designations with +30 indicating a completely clear product, was improved from +18.5 to +30. This result supported the conclusion drawn from the extensive analysis of MTBE that acenaphthylene and its derivatives, methylene indene and ethylidene indene and their derivatives, are the main color bodies in MTBE. A second experiment in which 15 cc of BH3/THF solution was added into 100 g of acenaphthylene/toluene solution, which was prepared in advance to have a concentration of 100 ppm, also supported this conclusion. The yellow color completely disappeared and the saybolt number became +30 in the second experiment.

Based on the assumption that the color bodies could be reduced by changing these unsaturated compounds into saturated compounds by hydrogenation, hydroboration and the like, prior technologies involving the hydrogenation of C=C bond were evaluated. However, experiments testing the possibility of hydrogenation of the color bodies to improve the color were unsuccessful. In fact, there was no change in the color of MTBE using prior technologies. After further analysis, it was found that prior hydrogenation technology was unsuccessful for removing color in MTBE due to the very poor solubility of lithium aluminum hydride (LiAlH4) to MTBE since the dissolved LiAlH4 can react with olefine. An experiment involving the hydrogenation of color bodies in MTBE was conducted in the presence of a palladium/carbon catalyst at room temperature and normal pressure. The catalyst amount was 3 g of palladium carbon (palladium content: 1%) for 120 of MTBE. After blowing hydrogen into MTBE for 30 minutes, the saybolt number was improved from +18.5 to +28.

Applying this information, it was found that the use of Pd/alumina catalyst with a circulation of hydrogen successfully improved the color of MTBE to +30 saybolt number. Based on these findings, the subject invention for improving color was developed to completely and economically remove the color from oxygenates used as gas blending components. While the following discussion is directed to a method for improving the color of MTBE, it will be readily understood that the subject invention is equally applicable to other oxygenates, such as by way of example, ETBE and TAME, for improving the color to +30 saybolt number.

The subject invention is directed to a process for removing color completely and economically from MTBE, ETBE and TAME utilizing a hydrogenation method for reducing the color bodies causing the color. The existing color bodies are hydrogenated in the presence of a catalyst containing at least one noble metal with a circulation of hydrogen and the reaction can proceed at room temperature and at normal pressure.

In the preferred embodiment of the subject invention, the color bodies in MTBE are hydrogenated using a trickle bed reactor packed with 0.5 wt % of Pd/r-alumina catalyst. While other general hydrogenation catalysts may be used, Pd/r-alumina is preferred because the carrier, alumina, adsorbs little and does not have any solubility to MTBE. For example, the Pd/C catalyst adsorbs much MTBE and adsorption heat appears at the new catalyst. Due to the heat of adsorption heat, the catalyst bed temperature may rapidly increase at the beginning of the operation to form a heat spot in the catalyst bed. This potential problem is avoided by utilizing Pd/r-alumina because the alumina carrier adsorbs little MTBE and produces little heat. The heat of adsorption produces is proportional to the amount of adsorbate. A low concentration of color bodies produces little heat.

In the preferred embodiment, MTBE is fed into the reactor with a circulation of hydrogen. At the trickle bed, hydrogen is a continuous phase in the reactor and can directly contact with the catalyst surface wherever the liquid fed into the reactor does not contact the surface. The fact that the hydrogen can directly contact the solid catalyst surface and adsorb on it is one reason for preferably utilizing a trickle bed reactor.

However, there are two kinds of resistances which may slow hydrogen transfer to the catalyst surface. One is the liquid layer, or liquid flow of the product fed into the reactor, which is formed physically on the catalyst surface. The second type of resistance is a boundary layer. The boundary layer may be defined as a very thin imaginary layer which is assumed to exist between the hydrogen gas phase and the solid surface of the catalyst. This boundary layer exists at the boundary between the gas phase and solid surface, even where no liquid layer exists, and becomes thinner as gas space velocity increases. In general, a thin boundary layer is desirable because a thicker boundary layer may slow the hydrogen transfer rate to the catalyst surface.

The circulation of hydrogen through the reactor increases the gas space velocity near the catalyst surface so that the boundary layer becomes thinner and allows the hydrogen to contact the catalyst surface. Thus, in the subject invention, a circulation of hydrogen through the reactor is preferable for helping to transfer the hydrogen through the boundary layer to the catalyst surface for adsorption. The adsorbed hydrogen reacts with olefin and the color bodies are hydrogenated thereby removing color from the product.

In the preferred embodiment, hydrogen is fed through a flow rate regulator from a hydrogen cylinder which is supplied commercially to keep the reactor pressure constant as hydrogen is consumed by its reaction with olefine. In addition to thinning the boundary layer for increasing the transfer of hydrogen to the catalyst surface, the circulation of hydrogen is important for gas distribution over the catalyst for utilizing the whole catalyst packed bed effectively. In general, the liquid flow of the product fed into the reactor flows through a pathway which offers the least amount of resistance to flowing, such as, for example, paths which are packed rough. Therefore, a slower flow rate often produces a "channeling phenomena" in which the fluid flows through only a part of the packed bed. Thus, when the flow rate is low, the fluid does not spread radially over the catalyst bed and results in not contacting with the whole of the packing. Without the circulation of hydrogen, the hydrogen flow would be very low and flow through only a part of the packed bed thereby causing the hydrogen transfer rate to be slowed. Thus, the circulation of hydrogen in the subject invention provides for a uniform flow of hydrogen which is very effective for adsorbing hydrogen and hydrogenating the existing color bodies. The supplied hydrogen should be 99.9% pure and must not include poisoning materials, such as carbon monoxide, harides, divalent sulfur compounds, amines, phosphine and the like since catalyst inhibition is caused by such poisons.

The hydrogenation of the color bodies of MTBE fed through the trickle bed reactor may proceed under room temperature and normal pressure. Typically, the temperature of MTBE as it is fed into the reactor is approximately 23 degrees Celsius and the pressure is close to 1 atm (5 mmH20). However, the hydrogenation method of the subject invention may be operated under a range of temperatures from 20 to 100 degrees Celsius and pressures ranging from 1 atm to 30 atm.

The feed rate into the reactor determines the catalyst amount and reactor volume. As the feed rate increases, the outlet product color gets worse because of the shortage of adsorbed hydrogen. However, it is generally known that the deterioration in the conversion of color bodies caused by an increased feed rate can be avoided by increasing the height of the catalyst bed. In fact, once the feed rate is known, the height of the catalyst bed can be selected to consistently produce MTBE with a +30 saybolt color number.

In the subject invention, once the feed rate is determined, the reactor diameter is calculated by a method, as is well known in the art, based on the flooding line which is dependent on the packing, catalysts in this case. The catalyst bed height may vary depending on the desired saybolt number and is calculated based on the reaction rate or mass transfer rate of hydrogen. Assuming that the desired number is +30, the catalyst bed height may be a maximum of approximately 2 meters.

While +30 saybolt number can be achieved at normal pressure, the height of the catalyst bed can be reduced by increasing the pressure at which the reaction proceeds. For example, by increasing the pressure to some point above normal pressure, the height of the catalyst bed should be decreased. This is due to the fact that the amount of hydrogen adsorbed on the catalyst is approximately proportional to the ambient hydrogen pressure. Therefore, in general, the higher the ambient pressure is, the lower the catalyst height is. However, it is economically viable to design a catalyst bed at a height to achieve +30 saybolt number where the pressure is close to the normal ambient pressure.

The process of the subject invention for achieving +30 saybolt number in oxygenates, such as MTBE, ETBE and TAME, requires the following steps: (1) feeding the oxygenate to a hydrogenation treater wherein existing color bodies in the oxygenate are hydrogenated in the presence of a catalyst and a circulation of hydrogen to remove color and (2) recovering a colorless oxygenate having a +30 saybolt number from the hydrogenation treater.

The following examples illustrate the preferred embodiment of the subject invention without limiting it.

EXAMPLE 1

Equipment
Reactor: Packed bed; 4 cm diameter, 55 cm height
Catalyst: 0.5 wt % Pd/r-alumina catalyst made in Engelhard; 3 mm diameter (sphere)
Catalyst amount: 467 g
Catalyst volume: 691 cm3
Packing density: 676 kg/m3
Hydrogen: cylinder; more than 99.9% pure
Operation pressure: 1 atm (5 mmH20)
Operation temperature: 22 degrees Celsius
Color specification: +30 saybolt number 55 ml of MTBE/hr was fed to the trickle bed reactor to which 6 1 of hydrogen per hour was fed at the same time. The saybolt number at the outlet improved from +17 to +27 ratably during 2.5 hours.

EXAMPLE 2

Using the same equipment and conditions as in Example 1, the feed rate was varied as shown in the table below. The initial and resulting saybolt numbers are also shown.

| Exp. No. | Feed Rate | Saybolt Number Improvement | |
| --- | --- | --- | --- |
| 1 | 100 g/hr | from +17 | to +26 |
| 2 | 57 | +17 | +27 |
| 3 | 110 | +17 | +26 |
| 4 | 53 | +17 | +26 |
| 5 | 255 | +17 | +25 |
| 6 | 55 | +17 | +27 |

EXAMPLE 3

MTBE having a +17 saybolt number is fed to the trickle bed reactor of Example 1 at 23 g/hr under the same conditions as in Example 1. The saybolt number was improved from +17 to +30.

EXAMPLE 4

Equipment
Reactor: Packed bed; 3 in diameter
Catalyst: 0.5 wt % Pd/r-alumina catalyst
Operating temperature: 22 degrees Celsius
Increased operating pressure: 28 psia
Color specification: +30 saybolt number MTBE having a +17 saybolt number is fed to the trickle bed reactor and the saybolt number improved to +30. The higher operating pressure reduces the catalyst bed height needed to achieve +30 saybolt number.

In another embodiment, the hydrogenation is accomplished using a stirred tank reactor with gas bubbling. A catalyst, preferably 2.5% Pd/r-alumina, is fed into the product in a slurry reactor with a stirrer. After stirring, the catalyst is separated by precipitation and new product is added in the same slurry reactor. Hydrogen is then bubbled, stirring the liquid phase at room temperature and normal pressure. While Pd/r-alumina is preferred, most of the general hydrogenation catalysts can be utilized. Specifically, the catalyst should contain at least one noble metal catalyst.

In addition, because too much shear in the stirred tank reactor may rip noble metals from a carrier, a non-carrier type of catalyst, such as raney-Ni, is often used at the stirred tank reactor. The reason noble metals can be ripped up by strong shear is because they are physically attached but not chemically bonded to the carrier. When noble metals are ripped up, they form small powders which may exit the reactor with the liquid. Thus, the catalyst concentration in the stirred tank reactor is reduced and the reaction rate is diminished.

The following examples illustrate an alternative embodiment of the subject invention without limiting it.

EXAMPLE 5

Equipment
Reactor: stirred tank reactor with catalyst suspended
Catalyst: 2.5 wt % Pd/r-alumina catalyst (powder)
Catalyst amount: 3 g
Hydrogen: cylinder; more than 99.9% pure
Operation pressure: normal
Operation temperature: 72 degrees Fahrenheit
Color specification: +30 saybolt number The catalyst was fed into 400 g of MTBE in the reactor with a stirrer having a volume of 500 cc and stirred for 30 minutes before the hydrogenation. After stirring for 30 minutes, there was little change in the saybolt number. This means that little adsorption of color bodies happened in the case of Pd/r-alumina catalyst. The catalyst was separated by precipitation from MTBE and then added to 120 g of untreated MTBE having +17 saybolt number in the same reactor. The hydrogen was bubbled for 5 minutes, stirring the liquid phase at the operating temperature and pressure noted above. The saybolt number improved from +17 to +30 in 5 minutes.

EXAMPLE 6

Equipment
Reactor: stirred tank reactor with catalyst suspended
Catalyst: 1.5 g of palladium/carbon (1% of palladium)
Hydrogen: cylinder; more than 99.9% pure
Operation pressure: normal
Operation temperature: 72 degrees Fahrenheit
Color specification: +30 saybolt number The catalyst was fed into 400 g of MTBE having yellow color. This liquid was stirred in 500 cc flask for 30 minutes at the above temperature and pressure before hydrogenation. This procedure is directed to the saturation of carbon adsorption sites with color bodies adsorbed on the carbon surface. Following that treatment, the catalyst was separated by precipitation and untreated MTBE having yellow color was added. The hydrogen was bubbled at the same conditions for 30 minutes. The yellow color was completely eliminated by this procedure.

EXAMPLE 7

ETBE with +7 saybolt number was treated with hydrogen in a flask which included catalyst composed of 2.5% palladium on alumina support. After 1 hour of treatment, ETBE with +7 saybolt color improved to +30.

The subject invention provides a new technology for removing color from oxygenates, such as MTBE, ETBE and TAME, through a hydrogenation method which is economical, can be operated under normal pressure and room temperature and results in a product with a +30 saybolt color number.

While specific embodiments and features of the invention have been disclosed herein, it will be readily understood that the invention encompasses all enhancements and modifications within the scope and spirit of the following claims.

What is claimed is:

1. A process for removing color completely and economically from oxygenates comprising the steps of:
   a. feeding the oxygenate to a hydrogenation reactor wherein existing color bodies in the oxygenate are hydrogenated in the presence of a catalyst and a circulation of hydrogen to remove the color; and
   b. recovering a colorless oxygenate from the hydrogenation reactor,
   c. wherein the hydrogenation reactor is provided with a catalyst containing at least one noble metal.

2. The process of claim 1, said oxygenate having a color intensity with an initial saybolt color number and wherein feeding the oxygenate to the hydrogenation treater increases the initial saybolt number from a lower number to a higher number.

3. The process of claim 2, wherein the saybolt number is increased to +30.

4. The process of claim 1, wherein the hydrogenation is carried out at a room temperature and at a normal pressure.

5. The process of claim 1, wherein the hydrogenation catalyst contains at least one noble metal.

6. The process of claim 5, wherein the noble metal is selected from the group consisting of ruthenium, rhodium, palladium, iridium, and platinum on the carrier selected from the group consisting of carbon, alumina, silica and zeolite.

7. The process of claim 4, wherein the hydrogenation reaction proceeds at approximately 22 degrees Celsius and approximately 1 atm.

8. The process of claim 1, wherein the hydrogenation reaction proceeds at a temperature ranging from 20 to 100 degrees Celsius and a pressure ranging from 1 atm to 30 atm.

9. The process of claim 6, wherein the catalyst is palladium/r-alumina.

10. The process of claim 1, wherein the oxygenate is selected from the group consisting of MTBE, ETBE or TAME.

11. The process of claim 1, wherein the hydrogenation reactor is a trickle bed reactor packed with a catalyst containing at least one noble metal.

12. The process of claim 1, wherein the hydrogenation reactor is a stirred tank reactor with a catalyst containing at least one noble metal suspended.

13. A process for removing color completely and economically from an oxygenate through a hydrogenation reaction for removing color bodies in the oxygenate comprising the steps of:
   a. selecting a feed rate of the oxygenate to a trickle bed reactor packed with a catalyst, said oxygenate having an initial color intensity;
   b. determining the reactor volume and the height of the catalyst bed based on the feed rate and the desired color intensity of the oxygenate;
   c. feeding the oxygenate to the trickle bed reactor;
   d. simultaneously feeding hydrogen to the trickle bed reactor; and
   e. recovering the oxygenate from the trickle bed reactor, said recovered oxygenate having an improved color intensity.

14. The process of claim 13, wherein the recovered oxygenate from the trickle bed reactor is colorless and has a +30 saybolt color number.

15. The process of claim 13, wherein the hydrogenation reaction proceeds at room temperature and at normal pressure.

16. The process of claim 13, wherein the hydrogenation catalyst contains at least one noble metal.

17. The process of claim 13, wherein the catalyst is 0.1 to 5 weight percent palladiumir-alumina.

18. The process of claim 13, wherein the hydrogenation reaction proceeds at a temperature ranging from 20 to 100 degrees Celsius and a pressure ranging from 1 atm to 30 atm.

19. The process of claim 14, a step further comprising selecting a pressure above normal pressure and reducing the height of the catalyst bed necessary to obtain the colorless oxygenate.

20. The process of claim 13, wherein the oxygenate is selected from a group consisting of MTBE, ETBE or TAME.

21. A process for removing color completely and economically from an oxygenate through a hydrogenation reaction for removing color bodies in the oxygenate comprising the steps of:
   a. feeding the oxygenate into a stirred tank reactor;
   b. feeding a catalyst into the oxygenate in the reactor, said oxygenate having an initial color intensity;
   c. adding hydrogen to the oxygenate and catalyst; and
   d. recovering an oxygenate from the stirred tank reactor, said recovered oxygenate having an improved color intensity.

22. The process of claim 21, wherein the oxygenate recovered from the stirred tank reactor is colorless and has a +30 saybolt color number.

23. The process of claim 21, wherein the hydrogenation catalyst contains at least one noble metal.

24. The process of claim 23, wherein the catalyst is 2.5 weight percent palladium/r-alumina.

25. The process of claim 21, wherein the catalyst is raney-Ni.

26. The process of claim 21, wherein the hydrogenation reaction proceeds at room temperature and at normal pressure.

27. The process of claim 21, wherein the oxygenate is selected from the group consisting of MTBE, ETBE or TAME.

* * * * *